United States Patent [19]

Kadi

[11] Patent Number: 4,530,233
[45] Date of Patent: Jul. 23, 1985

[54] METHOD AND APPARATUS FOR DISTINGUISHING BETWEEN DIFFERENT GAS OR GAS MIXTURES USING A FLOW TUBE

[75] Inventor: Frank J. Kadi, New Tripoli, Pa.

[73] Assignee: Air Products and Chemicals, Inc., Allentown, Pa.

[21] Appl. No.: 515,092

[22] Filed: Jul. 18, 1983

[51] Int. Cl.³ ............................................. G01N 7/00
[52] U.S. Cl. ........................................... 73/23; 73/30; 62/37; 62/125; 62/126
[58] Field of Search ............... 73/23, 32 R, 30; 137/2, 137/154, 171; 62/37, 125, 126

[56] References Cited

U.S. PATENT DOCUMENTS

| | | | |
|---|---|---|---|
| 1,633,352 | 6/1927 | Tate | 73/23 |
| 1,884,896 | 10/1932 | Smith | 73/23 |
| 2,263,335 | 11/1941 | Heinz | 73/51 |
| 2,331,208 | 10/1943 | Ludi | 73/290 |
| 2,619,107 | 11/1952 | Graham | 137/393 |
| 2,722,121 | 11/1955 | Fisher | 73/23 |
| 2,737,973 | 3/1956 | Kimmell | 137/407 |
| 2,954,841 | 10/1960 | Reistle | 183/77 |
| 3,086,386 | 4/1963 | Kapff | 73/23 |
| 3,181,574 | 5/1965 | Lenkey et al. | 141/130 |
| 3,334,513 | 8/1967 | Thomas | 73/23 |
| 3,340,699 | 9/1967 | Post et al. | 62/37 |
| 3,403,522 | 10/1968 | Henry | 62/37 |
| 3,447,359 | 6/1969 | Kapff | 73/23 |
| 3,517,685 | 6/1970 | Eastman | 137/81.5 |
| 3,526,276 | 9/1970 | Bennett et al. | 166/52 |
| 3,636,720 | 1/1972 | Krieve | 62/49 |
| 3,642,017 | 2/1972 | Homes | 137/81.5 |
| 3,817,085 | 6/1974 | Stubbs | 73/23 |
| 3,979,958 | 9/1976 | Janssen et al. | 73/290 |
| 4,033,171 | 7/1977 | Karas et al. | 73/23.1 |
| 4,186,590 | 2/1980 | Egorov et al. | 73/23 |

FOREIGN PATENT DOCUMENTS

| | | | |
|---|---|---|---|
| 0036285 | 9/1981 | European Pat. Off. | 73/23 |
| 148272 | 12/1954 | Fed. Rep. of Germany . | |
| 1089192 | 9/1960 | Fed. Rep. of Germany | 73/23 |
| 2445892 | 4/1976 | Fed. Rep. of Germany . | |
| 3010622 | 9/1981 | Fed. Rep. of Germany | 73/23 |
| 3107617 | 2/1982 | Fed. Rep. of Germany . | |
| 137132 | 10/1981 | Japan | 73/23 |
| 713322 | 8/1954 | United Kingdom . | |
| 779824 | 7/1957 | United Kingdom . | |
| 1229446 | 4/1971 | United Kingdom . | |
| 1360405 | 7/1974 | United Kingdom . | |
| 263939 | 8/1970 | U.S.S.R. | 73/23 |
| 439731 | 1/1975 | U.S.S.R. | 73/23 |
| 481814 | 10/1975 | U.S.S.R. | 73/23 |
| 248275 | 11/1979 | U.S.S.R. . | |

OTHER PUBLICATIONS

F. Biermans and J. Nihoul, A Simple and Continusos Level Indicator for Liquefied Gases, 3/15/62, 243, Research and Technical Note.
W. A. Wildhack, A Versatile Pneumatic Instrument Based on Critical Flow, Jan. 1950, vol. 21, No. 1, pp. 25–30, The Review of Scientific Instruments.

Primary Examiner—Stephen A. Kreitman
Attorney, Agent, or Firm—James C. Simmons; E. Eugene Innis

[57] ABSTRACT

A flow tube to distinguish between different gases or gas mixtures flowing through the tube, the tube being sized so that a first or control gas or gas mixture is selected and the properties of the control gas or gas mixture are such that when the control gas or gas mixture flows through the tube a shock wave of a given magnitude is formed at the discharge end of the tube. A second gas flowing in the tube forms a shock wave of different magnitude at the discharge end of the tube; detection of a difference in the magnitude of the shock wave being the operative distinguishing means.

8 Claims, 4 Drawing Figures

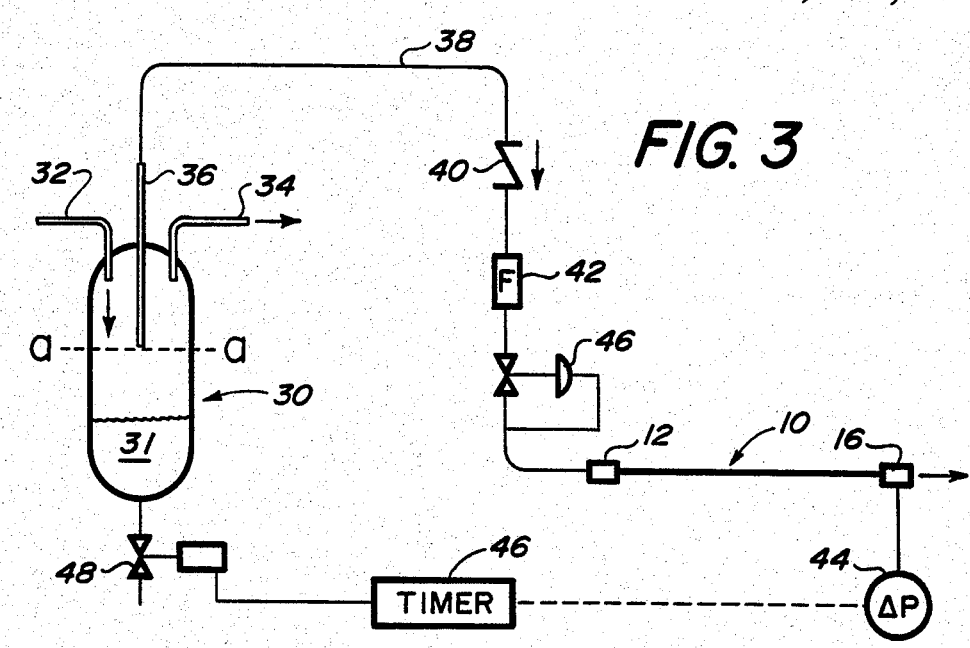
FIG. 3
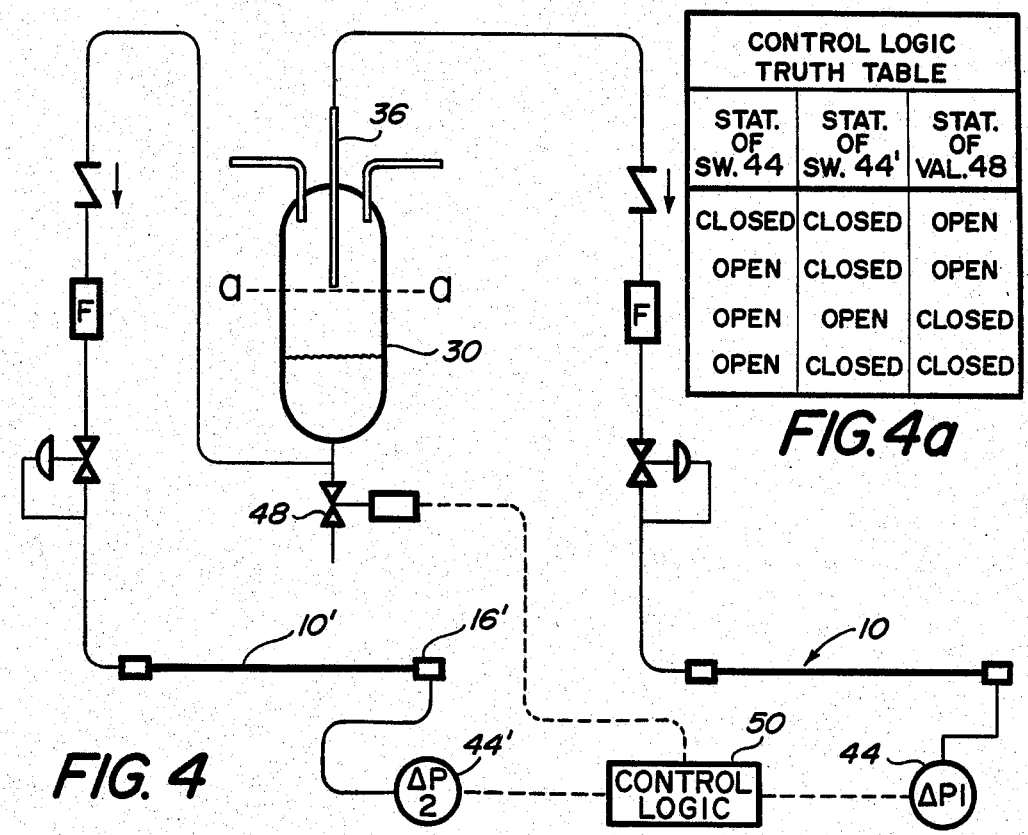
FIG. 4
FIG. 4a

METHOD AND APPARATUS FOR DISTINGUISHING BETWEEN DIFFERENT GAS OR GAS MIXTURES USING A FLOW TUBE

TECHNICAL FIELD

This invention pertains to methods and apparatus for distinguishing between different gases or gas mixtures by means of a flow tube. Detection or differentiation of different species of gases or gas mixtures is a method usable for controlling process operations such as in an apparatus for purifying helium.

BACKGROUND OF THE PRIOR ART

Various prior art devices have been developed to distinquish between different gas species or gas mixtures in process control apparatus. For example, U.S. Pat. No. 4,186,590 discloses an apparatus which relies on attainment of supersonic velocity in a convergent/divergent Laval nozzle to detect impurities in a gas stream The presence of impurities is detected by the total head of fluid downstream of the Laval nozzle as influenced by change in axial position of a shock wave.

British Pat. No. 713,322 discloses a device which utilizes two flow restrictions with a downstream nozzle in the critical flow path, thus requiring the use of two nozzles.

U.S. Pat. No. 3,642,017 discloses a device which dtects the position of a shock wave, U.S. Pat. No. 3,340,699 discloses the use of a float to detect liquid level in a helium purifier, and U.S. Pat. Nos. 1,360,405 and 3,181,574 disclose the use of timing mechanisms in a process apparatus to drain the sump of a device such as a flash tank condenser or the like.

U.S. Pat. Nos. 2,263,335, 3,334,513, 4,033,171, and 1,633,352 disclose devices that use laminar flow devices to differentiate between gas species.

BRIEF SUMMARY OF THE INVENTION

The present invention pertains to a flow tube devioe which can be utilized to distinquish between different gases or gas mixtures flowing throuqh the tube. The tube is constructed and arranged (sized) so that a first or control gas flowing through the tube creates a standing expansion or shock wave of a given magnitude formed at the exit of the flow tube. A different gas or gas mixture flowing through the same tube will create a standing expansion or shock wave of different magnitude and the difference between the magnitude of the shock waves can be detected and utilized to control a process apparatus. For example, such a device can be utilized in association with a condenser in a helium purification apparatus to detect the level of condensate in a condenser and thus vent or dump the condensate from the condenser.

BRIEF DESCRIPTION OF THE DRAWING

FIG. 3 is a schematic diagram showing the use of the flow tube as a liquid level controller for the air condenser in helium purification apparatus.

FIG. 4 is an alternate embodiment of the apparatus of FIG. 3 utilizing two flow tube analyzers.

DETAILED DESCRIPTION OF THE PREFERRED EMBODIMENT

In the purification of helium most process schemes employ a condenser where air is liquefied and separated from the helium gas. Such condensers or purifiers normally operate at approximately 1400 psig (9652 kpa) and $-320°$ F. ($-196°$ C.). Conventional purifiers use electronic devices to detect the liquid level in the condenser, such devices having short service life at the conditions stated above.

In order to overcome the problems noted above a flow tube such as shown in FIG. 1 was devised in order to distinguish between different gases or gas mixtures flowing through the tube. The device of FIG. 1 can function provided the gases being differentiated differ sufficiently from one another with respect to the ratio of specific heats, $\alpha$, and the specific gas constant R. Such a device can be used to obtain an estimate of the percentage composition of a mixture of any of these two gases. For example, gas combinations which would be likely candidates for this technique would be helium/nitrogen and helium/oxygen.

Figure 1:
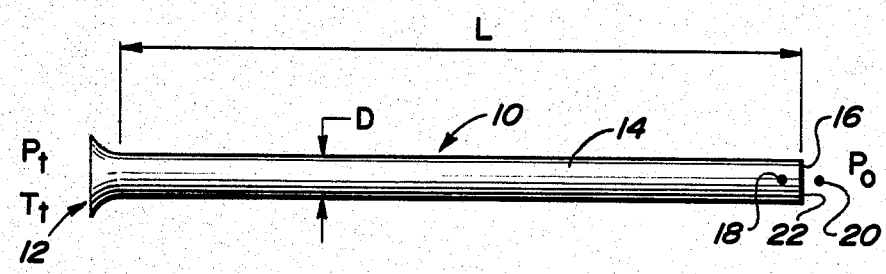
FIG. 1 is a schematic diagram of a flow tube according to the present invention.

The device of FIG. 1 operates based upon the difference in the strength of a standing expansion or shock wave which is formed at the exit of the flow tube when different gases are passed through the tube. In the case of the device of FIG. 1, the strength of the shock front is determined by the magnitude of the pressure drop across the shock. The gas analyzer flow tube 10 of FIG. 1 includes an inlet section 12 at which both the inlet pressure $P_t$ and temperature $T_t$ are constant. While FIG. 1 shows the inlet section 12 as a convergent nozzle, this assumption was made to facilitate the mathematical treatment of the device; it is not essential to its operation. Tube 10 consists of a flow circuit of uniform cross-sectional area 14 characterized by a hydraulic diamater D, and a flow length, L. The sizing of flow tube 10 consists of selecting the tubing parameters $P_t$, $T_t$, D, and L such that the gas with a tendency for establishing the weakest shock wave will be made to flow through the tube such that the shock wave is just at the verge of forming at the exit 16 of tube 10. Normally the gas that is selected for this calculation will be called the first or control gas. As a result of this construction, a pressure difference between points 18 and 20 measured at location 22 of tube 10 of FIG. 1 will be approximately 0. Thus, if a second gas or gas mixture is passed through tube 10 at the same inlet pressure and temperature, the establishment of a shock wave at the exit 16 of tube 10 will bring with it a jump in the pressure difference between points 18 and 20. Thus, a distinction between the two gases can be made by monitoring a differential pressure indicator located at 22 of FIG. 1.

The phenomena utilized in the flow tube gas analyzer depends upon choked flow in the tube (Fanno flow), the equations for which are well known and can be found in any text on compressible fluid mechanics. The equations which are required to completely define the present device include a first equation governing the reversible adiabatic flow of an ideal gas in a convergent inlet nozzle as follows:

$$\frac{\dot{m}\sqrt{RT_t}}{AP_t} = \sqrt{\gamma}\, M_1 \left[1 + \frac{\gamma-1}{2} M_1^2\right]^{-\frac{\gamma+1}{2(\gamma-1)}}$$

where
A is the area of the nozzle throat which is also equal to the cross-sectional area of flow tube.

$M_1$ is the Mach number at the nozzle throat and m is mass flow rate.

The equation which characterizes the pressure ratio $P_0/P_t$ required to achieve sonic flow of an ideal gas at the exit of a reversible adiabatic flow tube is given by:

$$\frac{\dot{m}\sqrt{RT_t}}{AP_t} = \frac{P_o}{P_t}\sqrt{\gamma}\sqrt{\frac{\gamma + 1}{2}}$$

The equation which defines the diameter, D, and length, L, required to achieve chocked flow of an ideal gas at the exit of a tube, assuming an adiabatic reversible flow with a mach number, $M_1$, at the inlet is:

$$4\bar{f}\frac{L}{D} = \frac{1 - M_1^2}{\gamma M_1^2} + \frac{\gamma + 1}{2} \ln\left[\frac{\frac{\gamma + 1}{2} M_1^2}{1 + \frac{\gamma + 1}{2} M_1^2}\right]$$

Where $\bar{f}$ is the friction factor of the tube defined by the tube Reynold's number.

Figure 2:
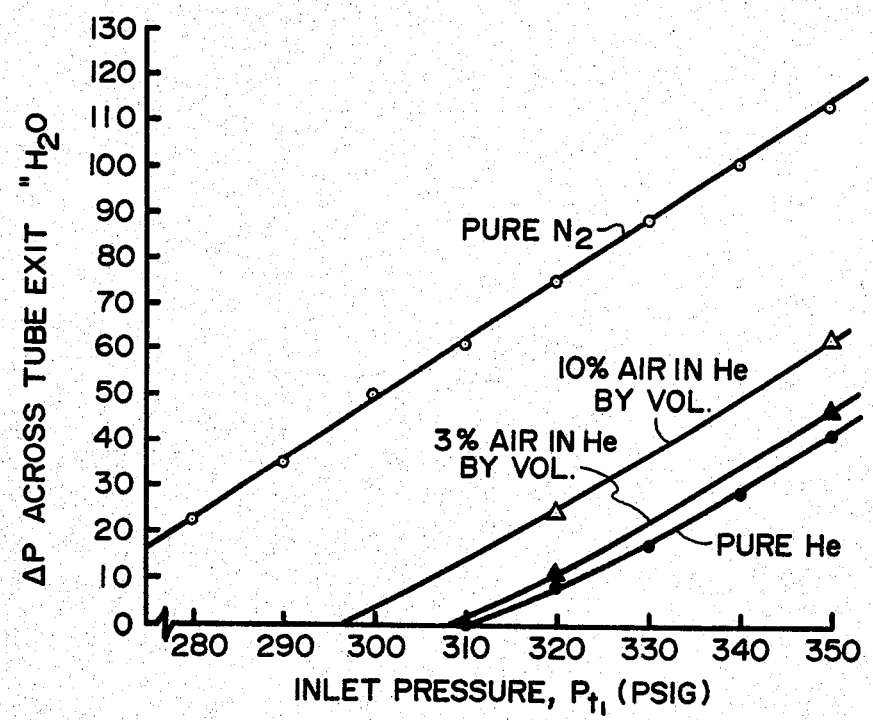
FIG. 2 is a plot of inlet pressure versus pressure differential across the exit tube of FIG. 1 for various gases and gas mixtures.

A device according to FIG. 1 was fabricated and successfully tested. The prototype device consisted of a 39.25 in. (99.7 cm) long capillary tube with a 0.012 in. (0.305 mm) inside diameter. A pressure tap at the exit 16 of tube 10 was located approximately 1/16 in. upstream from exit 16. Tests were performed utilizing pure helium, pure nitrogen, and 3% and 10% of air by volume in helium mixtures. The inlet pressure was varied and the pressure difference across the tube exit, ($P_0$–$P_{18}$), was monitored for each mixture. The results of these measurements are illustrated in FIG. 2. FIG. 2 indicates that if the inlet pressure $P_t$ was fixed at 310 psig (2137 kpa) then the pressure difference across the exit of flow tube 10 would go from 0 in. (0 cm) of water to 62 in. (157.5 cm) of water when the gas passing through the tube changed from pure helium to pure nitrogen.

Analysis of the flow equations for choked flow in a tube indicates that for the gases tested, there is a potential for almost twice the shift in the pressure differential shown in FIG. 2.

FIG. 3 illustrates the application of the apparatus of FIG. 1 as a liquid level controller for a condenser associated with a helium purifier. In the apparatus of FIG. 3, a mixture of liquid air and helium enters a condenser 30 through a conduit 32. The liquid condensate separates and collects at the bottom of the condenser with the remaining gaseous helium at −320° and air exiting the condenser through conduit 34 for further processing. As the helium purifier operates, eventually the liquid condensate level approaches that shown as level a—a of FIG. 3. During operation of the condenser 30 a gas sample is withdrawn at a continuous low flow rate through a sample tube 36. The gas sample which is typically at 1400 psig (9652 kpa) passes through an elongated conduit 38 which is of a highly conductive material and of a length sufficient to allow the cold gas leaving condenser 30 to warm up to ambient temperature. The warmed gas passes through a check valve 40, a filter 42 and enters a pressure regulator 46. Pressure regulator 46 maintains a fixed inlet pressure $P_t$ at the inlet 12 of flow analyzer tube 10. Check valve 40 is included to prevent back diffusion of water vapor and air into condenser 30 when its pressure is reduced.

When the level of air condensate in condenser 30 is below sampling point a—a, the gas flowing through flow tube analyzer 10 is 98% or better helium by volume, therefore, the pressure differential (ΔP) measured by a differential pressure switch 44 is approximately or very close to 0. When the condensate level reaches a—a, the gas passing through the flow tube analyser 10 suddenly changes to nearly 100% air and the pressure switch is exposed to a pressure differential in excess of 60 in. (152.4 cm) of water pressure as shown in FIG. 2. The pressure increase closes an electrical contact on switch 44 which begins a timing period on timer 46, the net effect of which is that timer 46 opens a condensate dump valve 48 for a period of time sufficient to empty the liquid air from condenser 30. Prior to completion of the dump, gas moving through the flow tube analyser 10 changes back to almost pure helium and pressure switch 44 resets.

Unlike current state-of-the-art level controllers, the flow tube analyzer described above allows placement of all the key system components at room temperature and pressure. This configuration allows for very easy adjustment and repair of the device and eliminates most of the restriction on physical size. The only component which remains in the condenser environment is the gas sampling capillary tube 36.

An alternate control scheme using two flow tube analyzers is shown in FIG. 4. In the apparatus of FIG. 4 a second flow tube analyser 10′ is utilized to replace the timer 46 of the device of FIG. 3. During most of the entire condenser fill phase, flow tube analyzer 10′ has nearly 100% air flowing through it. Thus, a shock wave is created at the exit 16′ of flow tube analyzer 10′ which generates a large pressure differential $\Delta P_2$, which closes switch 44′. As the level of condensate rises in vessel 30, sample tube 36 eventually conducts nearly 100% air to flow analyzer tube 10 which causes closure of switch 44. The action of the condenser dump valve 48 is controlled by logic control module 50 in accordance with the control logic truth table shown on the drawing as FIG. 4. Logic control module 50 can be any integrated circuit or relay logic device which operates in accordance with the logic truth table shown in FIG. 4a. The advantage of this control circuit over that shown in FIG. 3 is the independence from the time required to dump the condensate from vessel 30.

Having thus described my invention what is desired to be secured by Letters Patent of the United States is set forth in the appended claims.

What is claimed is:

1. An apparatus for distinguishing between different gases or gas mixtures flowing ad seriatum through a tube comprising in combination:

a flow tube having an inlet section and an outlet section said tube being so constructed and arranged that a first or control gas flowing through the tube will establish a shock wave of a given magnitude at the exit of the tube;

means for introducing gas to the inlet of said flow tube; and means for measuring the pressure differential across the exit of said flow tube; whereby when said first or control gas flows through said tube said exit pressure differential is near zero and when the second or other gas or gas mixture flows through said tube said pressure differential is significantly higher than measured with said first or control gas.

2. An apparatus according to claim 1 wherein said means for measuring the pressure difference includes means to activate other process equipment in response to detection of a second gas flowing through said tube.

3. In a helium purifier of the type wherein a mixture of helium and liquefied air is introduced into a condenser for separation of the gaseous helium from the liquefied air, the improvement comprising in combination:
   a flow tube disposed downstream in the exit line from the condenser said tube being so constructed and arranged so that when helium is flowing through said tube from an inlet to an outlet of said tube, said helium will be at the verge of forming a shock wave at the outlet of said tube and the pressure difference across the outlet of said tube during helium flow will be approximately zero;
   means for measuring the pressure differential across the exit of the flow tube; whereby when air enters said flow tube the pressure differential across the exit of said flow tube increases significantly; and
   means to remove condensate from said condenser, said means activated by the increased pressure detected across the outlet of said flow tube.

4. A helium purifier according to claim 3 wherein a conduit is included between said condenser and said flow tube is of a sufficient length to allow gas or condensate leaving said condenser to warm to ambient temperature prior to entering said flow tube.

5. A helium purifier according to claim 3 wherein said means to remove condensate from said condenser includes a dump valve on said condenser controlled by a timer activated by a switch closed by the increase pressure detected across the exit of said flow tube.

6. A helium purifier according to claim 3 wherein said means to remove condensate from said condenser includes a second flow tube disposed in a line to continuously receive vaporized condensate from said condenser, said second flow tube including a pressure sensing device connected to a logic controller which is also connected to said first flow tube pressure detecting means, whereby said logic controller controls a dump valve on said condenser in response to preset conditions.

7. A method for distinguishing between different gases or gas mixtures flowing through a process apparatus or conduits associated therewith comprising the steps of:
   selecting a first or control gas or gas from which the other or second gases or gas are to be distinguished and utilizing the of the first gas or gas mixture to construct a flow tube so dimensioned that as the first gas or gas mixture exits said tube a weak shock wave is at the verge of forming and a near zero pressure differential is established across the outlet of said tube; and
   interspersing said tube in the process apparatus or conduits at a point where the difference is to be detected.

8. A method according to claim 7 wherein a further step of detecting a change in the differential pressure across the outlet of the tube indicates the presence of a different gas or gas mixture in said process apparatus.

* * * * *